United States Patent [19]

Maruyama et al.

[11] 3,960,873

[45] June 1, 1976

[54] 1-PHENYLTHIOPROPYL-4-HYDROXY-4-PHENYL PIPERIDINES

[75] Inventors: Isamu Maruyama, Minoo; Hisao Yamamoto, Nishinomiya; Masaru Nakao, Toyonaka; Shigeru Sakai, Toyonaka; Kikuo Sasajima, Toyonaka; Sumio Kitagawa, Moriguchi; Shigeho Inaba, Takarasuka, all of Japan

[73] Assignee: Sumitomo Chemical Co., Ltd., Osaka, Japan

[22] Filed: June 21, 1974

[21] Appl. No.: 481,796

Related U.S. Application Data

[62] Division of Ser. No. 145,065, May 19, 1971, Pat. No. 3,845,057.

[30] Foreign Application Priority Data

| May 20, 1970 | Japan | 45-43555 |
|---|---|---|
| May 20, 1970 | Japan | 45-43556 |
| May 22, 1970 | Japan | 45-44303 |
| May 23, 1970 | Japan | 45-44289 |
| May 29, 1970 | Japan | 45-46668 |
| June 15, 1970 | Japan | 45-52254 |
| June 18, 1970 | Japan | 45-53276 |
| June 26, 1970 | Japan | 45-56305 |
| June 29, 1970 | Japan | 45-57541 |
| July 6, 1970 | Japan | 45-59300 |
| July 17, 1970 | Japan | 45-63091 |

[52] U.S. Cl. ......................................... 260/293.73
[51] Int. Cl.$^2$ ..................................... C07D 211/52
[58] Field of Search .................. 260/293.73, 293.74

[56] References Cited
UNITED STATES PATENTS

| 2,846,437 | 8/1958 | Elpern | 260/293.73 |
|---|---|---|---|
| 2,850,500 | 9/1958 | Elpern | 260/293.73 |
| 3,052,683 | 9/1962 | Carabateas | 260/293.73 |
| 3,356,657 | 12/1967 | Walker | 260/293.73 |
| 3,674,799 | 7/1972 | Edenhofer et al. | 260/293.73 |

OTHER PUBLICATIONS

Porszasz et al., Arzneimittel–Forsch, 14: 1343–1349 (1964).

Wasserman et al., C.A. 57: 12428h (1962).

*Primary Examiner*—Sherman D. Winters
*Attorney, Agent, or Firm*—Stevens, Davis, Miller & Mosher

[57] ABSTRACT

Novel N-substituted heterocyclic derivatives represented by the formula,

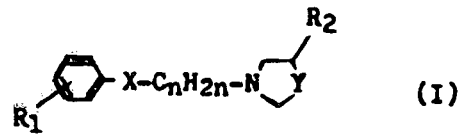

wherein $R_1$ is hydrogen atom, lower alkyl, lower alkoxy, nitro, halogen or trifluoromethyl group; $R_2$ is hydrogen atom or lower alkyl group; X is sulfur atom, sulfinyl or sulfonyl group; Y is

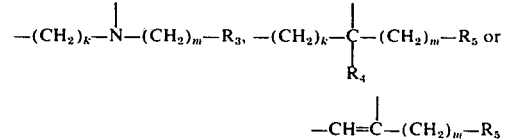

group (wherein $R_3$ is phenyl or substituted phenyl group; $R_4$ is hydrogen atom, hydroxy, lower alkyl, lower alkoxy, lower alkanoyl, lower alkanoyloxy, carbamoyl, N-(lower alkyl)-carbamoyl or N,N-di(lower akyl)-carbamoyl group; $R_5$ is hydrogen atom, morpholino, pyrrolidinyl, piperidinyl, hexamethylenimino, lower alkyl, cyclo(lower alkyl), cyclo(lower alkyl)-(lower alkyl), hydroxy-(lower alkyl), (lower alkoxy)-(lower alkyl), phenyl or substituted phenyl group; $k$ is 0 or 1 and $m$ is 0, 1 or 2); and $n$ is 3 or 4, and pharmaceutically acceptable salts thereof, which have excellent tranquillizing, anti-psychotonic, anti-emotional, anti-convulsive, anti-psychosis, sedative, analgesic or anti-hypertensive activities.

3 Claims, No Drawings

1-PHENYLTHIOPROPYL-4-HYDROXY-4-PHENYL PIPERIDINES

This is a division of application Ser. No. 145,065, filed May 19, 1971, now U.S. Pat. No. 3,845,057.

The present invention relates to novel N-substituted heterocyclic derivatives, pharmaceutically acceptable salts thereof and preparation thereof. More particularly, the present invention pertains to novel N-substituted heterocyclic derivatives represented by the formula,

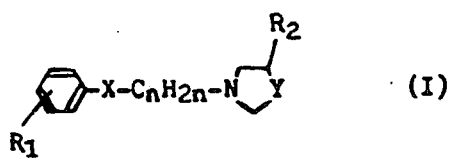

wherein $R_1$ is hydrogen atom, lower alkyl, lower alkoxy, nitro, halogen or trifluoromethyl group; $R_2$ is hydrogen atom or lower alkyl group; X is sulfur, sulfinyl or sulfonyl group; Y is

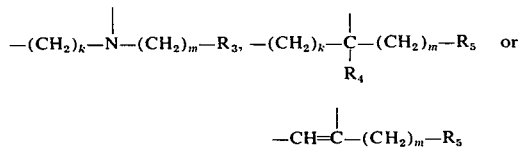

group (wherein $R_3$ is phenyl or substituted phenyl group; $R_4$ is hydrogen atom, hydroxy, lower alkyl, lower alkoxy, lower alkanoyl, lower alkanoyloxy, carbamoyl, N-(lower alkyl)carbamoyl or N,N-di(lower alkyl)carbamoyl group; $R_5$ is hydrogen atom, morpholino, pyrrolidinyl, piperidinyl, hexamethylenimino, lower alkyl, cyclo(lower alkyl), cyclo(lower alkyl)-(lower alkyl), hydroxy-(lower alkyl), (lower alkoxy)-(lower alkyl), phenyl or substituted phenyl group; $k$ is 0 or 1 and m is 0, 1 or 2); and $n$ is 3 or 4, and the pharmaceutically acceptable acid addition and quarternary ammonium salts thereof, and to processes for the preparation of the same.

As used herein, the term "lower alkyl", "lower alkoxy", and "lower alkanoyl" means such groups containing from one to seven carbon atoms which can be either straight or branched, and thus the lower-alkyl moiety represents, for example, methyl, ethyl, n-propyl, isopropyl, isobutyl, n-hexyl, and the like, and lower-alkanoyl represents, for example, formyl, acetyl, propionyl, -methylhexanoyl, and the like. The term "halogen" includes all four halogens, i.e., iodine, bromine, chlorine and fluorine. The term "substituted-phenyl" means that the benzene ring thereof can bear one or more substituents; and the substituent in the benzene ring can be halogen such as fluorine, chlorine, bromine and iodine; nitro, trifluoromethyl, $C_{1-7}$ alkoxy and $C_{1-7}$ alkyl. Thus, the substituted-phenyl include fluorophenyl, chlorophenyl, bromophenyl, methoxyphenyl, iodophenyl, tolyl, nitrophenyl, trifluoromethylphenyl, dichlorophenyl, methyl-isopropylphenyl, difluorophenyl; dimethoxyphenyl, methyl-chlorophenyl, methyl-bromophenyl, trichlorophenyl, trimethoxyphenyl and the like.

The group of the formula, $-C_nH_{2n}-$, represents a straight chain or branched chain alkylene group having up to 4 carbon atoms, and includes, for example, trimethylene, 1-methyltrimethylene, 2-methyltrimethylene and tetramethylene groups.

The N-substituted heterocyclic compounds of this invention form pharmaceutically acceptable salts with a variety of organic and inorganic acids. Such salts are formed with such acids as sulphuric, phosphoric, hydrochloric, hydrobromic, hydriodic, sulphamic, citric, lactic, maleic, malic, succinic, tartaric, cinnamic, acetic, benzoic, gluconic and ascorbic acids. They also form quaternary ammonium salts with a variety of organic esters of sulphuric, hydrohalic, and aromatic sulphonic acids. Among such esters are methyl chloride and bromide, ethyl chloride, propyl chloride, butyl chloride, isobutyl chloride, benzyl chloride and bromide, phenethyl bromide, naphthylmethyl chloride, dimethyl sulphate, diethyl sulphate, methyl benzenesulphonate, ethyl toluene-sulphonate, ethylene chlorohydrin, propylene chlorohydrin, allyl bromide, methallyl bromide and crotyl bromide.

It has surprisingly been found by the present inventors that the compounds represented by the formula (I) above and their pharmaceutically acceptable salts have valuable pharmacological properties in particular excellent tranquillizing, antipsychotonic, anti-emotional, anti-convulsive, anti-psychosis, sedative, analgesic or anti-hypertensive activities.

Each of the pharmaceutically active compounds of this invention may be, e.g., incorporated, for oral administration, in a tablet as the sole active ingredient. A typical tablet is constituted by from 1 to 2 per cent binder, e.g. tragacanth; from 3 to 10 per cent lubricant, e.g. talcum; from 0.25–1.0 per cent lubricant, e.g. magnesium stearate; an average dose of active ingredient; and q.s. 100 per cent of filler, e.g. lactose. The usual oral dosage is 1–100 mg per os daily.

Accordingly, an object of the present invention is to provide novel and useful N-substituted heterocyclic derivatives and salts thereof which have excellent pharmacological properties. Another object is to provide processes for producing such novel and useful N-substituted heterocyclic derivatives and salts thereof. A further object is to provide pharmaceutical composition containing such novel and useful N-substituted heterocyclic derivatives or salts thereof. Other objects and merits of the present invention will be apparent from the following descriptions.

In order to accomplish these objects the present invention provides novel N-substituted heterocyclic derivatives represented by the formula (I) and acid addition salts thereof.

According to the present invention, the novel N-substituted heterocyclic derivatives represented by the formula (I) may be prepared by a variety of methods.

One method for producing the N-substituted heterocyclic derivatives of the formula (I) comprises reacting a compound represented by the formula,

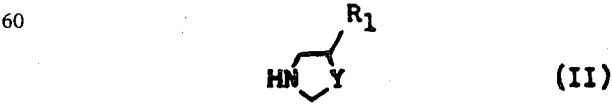

wherein $R_1$ and Y are as defined above, or an alkali metal salt thereof, with a reactive ester of a compound represented by the formula,

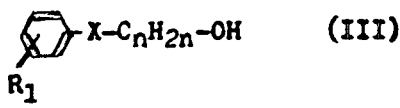

(III)

wherein $R_1$, X and n are as defined above.

Examples of reactive esters include hydrohalic acid esters such as the chlorides, bromides and iodides and sulfonic acid esters such as methanesulfonate, p-toluenesulfonate, β-naphthalenesulfonate and trichloromethanesulfonate.

The metal salt of the compound of the formula (II) may be prepared by treating the compound of the formula (II) with an alkaline agent in a suitable solvent or solvent mixture, if necessary, while cooling or heating, and/or in the atmosphere of an inert gas, for example, nitrogen. Examples of the alkaline agents include alkali metal hydride such as sodium hydride or lithium hydride, alkali metal hydroxide such as potassium hydroxide, alkali metal amide such as sodium amide, potassium amide or lithium amide, alkyl alkali such as butyl lithium, phenyl alkali such as phenyl lithium, alkali metal alcoholate such as sodium methylate, sodium ethylate, potassium tertiary-butoxide or the like. A metal salt-forming reactant may also be added to the mixture of the two reactants, preferably a solution thereof, forming the alkali metal salt in situ and bring about the desired reaction.

The reaction may generally be effected in an organic solvent or solvent mixture. Suitable solvents include benzene, toluene, xylene, dimethylformamide, dimethylacetamide, diphenyl ether, diglyme, dimethyl sulfoxide, methyl ethyl ketone, N-methyl pyrrolidone and the like, and a solvent mixture thereof. The reaction may be carried out at a temperature within a range between about room temperature and the boiling point of the solvent employed.

When a free compound of the formula (II) is used, the reaction may be preferably carried out in the presence of an acid acceptor to catch the acid which is liberated during the course of the reaction. Suitable acid acceptors include alkali metal hydroxide, carbonates, bicarbonates and hydrides, and organic tertiary amines such as triethyl amine, tributyl amine, N-alkyl piperidine, N-alkyl morpholine, pyridine, quinoline, diethyl aniline, dimethyl aniline and the like. An excess of the compound of the formula (II) may be also used as an acid acceptor.

The compounds of the formula (I) wherein X is sulfur or sulfonyl can also be prepared by treating compounds represented by the formula,

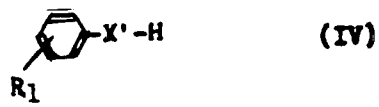

(IV)

wherein $R_1$ is as defined above and X' is sulfur or sulfonyl, with a compound represented by the formula,

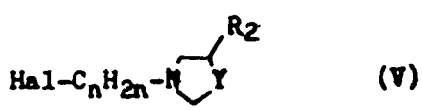

(V)

wherein $R_2$, Y and n are as defined above; and Hal is halogen.

The reaction can be carried out in the absence or presence of an acid acceptor, the purpose of which is to take up the hydrogen halide split out during the course of the reaction. Suitable acid acceptors include sodium carbonate, potassium carbonate, sodium bicarbonate, sodium hydroxide, potassium hydroxide, sodium hydride, potassium hydride, triethyl amine and the like. The reaction is carried out in the presence of a solvent or solvent mixture. Suitable solvents include benzene, toluene, xylene, dimethylformamide, lower alkanols such as methanol and ethanol, acetone, butanone, dioxane, tetrahydrofuran and the like, and a mixture thereof. The reaction may be carried out at a temperature within a range between about room temperature and the boiling point of the solvent employed.

The compounds of the formula (I), wherein X is sulfur, n is 3 to 4 and $R_4$ is hydrogen atom, hydroxy, lower alkyl or lower alkoxy group, can be also prepared from the corresponding compounds represented by the formula,

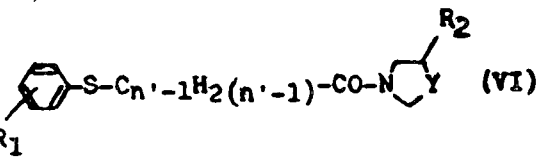

(VI)

wherein $R_1$ and $R_2$ are as defined above, $n'$ is 3 or 4 and $Y'$ is

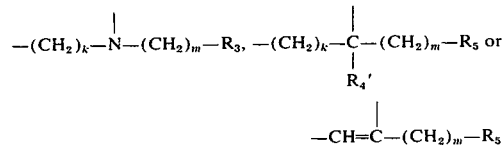

group, (wherein $R_3$, $R_5$, $k$ and $m$ are as defined above, and $R_4'$ is hydrogen atom, hydroxy, lower alkyl or lower alkoxy group) by reduction. The compounds of the formula (VI) can be reduced with a suitable reducing agent such as alkali metal in alcoholic solvent, hydrogen in the presence of a catalyst, metal hydride complexes which include metal aluminum hydride, boron hydride and their mixture with aluminum chloride, ferric chloride, boron trifluoride, hydrogen chloride or the like. An electrolytic reduction can also be used for the purpose. A preferable reducing agent is selected from metal hydride complexes such as lithium aluminum hydride and the mixture of, for example, lithium aluminum hydride and aluminum chloride, sodium borohydride and aluminum chloride, sodium borohydride and boron trifluoride and the like. The reaction is generally carried out in the presence of a solvent or solvent mixture. The choice of solvent depends on the reducing agent employed, and solvent is selected from the group consisting of water, ethanol, ether, tetrahydrofuran, dioxane, N-ethylmorpholine and the like. The reaction is carried out a room temperature, at a temperature below room temperature or at an elevated temperature.

The compounds of the formula (I) wherein X is sulfur can be converted to the compounds wherein X is sulfinyl or sulfonyl by treating such compounds with an oxidizing agent. As the oxidizing agent, there is used, for example, chromic acid, nitric acid, hydrogen peroxide, organic peracid (e.g. performic, peracetic, perbenzoic or m-chloroperbenzoic acid), sodium periodate, potassium periodate, persulfate, selenium dioxide, lead tetracetate, manganese dioxide or ruthenium tetraoxide. The reaction is advantageously effected in the presence of a solvent, in general. The choice of the solvent depends on the oxidizing agent employed, and the solvent is selected from the group consisting of water, chloroform, carbon tetrachloride, acetone, acetic acid, formic acid, sulfuric acid, pyridine, dioxane, benzene, toluene, ether, ethyl acetate, methanol, ethanol and the like, and a mixture thereof. The reaction temperature varies depending on the oxidizing agent employed. Generally, the reaction proceeds readily at room temperature, but the temperature may be higher or lower, for example, 0° – about 100°C or a boiling point of the solvents, preferably 10° – 60°C, as necessary to effect the desired control of the reaction.

The thus obtained N-substituted heterocyclic compounds of the formula (I) in free base form are converted to the acid-addition salt form by interaction of the base with an acid. In like manner, the free bases can be regenerated from the acid-addition salt form in the conventional manner, that is, by treating the salts with strong aqueous bases, for example, alkali metal hydroxides, alkali metal carbonates and alkali metal bicarbonates. The bases thus regenerated can then be interacted with the same or a different acid to give back the same or a different acid-addition salt. Thus the novel bases and all of their acid-addition salts are readily interconvertible.

The quaternary ammonium salts are obtained by the addition of esters of strong acids to the free base form of the compounds, said esters having a molecular weight less than about 200. A preferred class of esters comprises alkyl, alkenyl, and monocarbocyclic aryl-lower-alkyl esters of strong inorganic acids or organic sulfonic acids, including such compounds as methyl chloride, methyl bromide, methyl iodide, ethyl bromide, propyl chloride, allyl chloride, allyl bromide, methyl sulfate, methyl benzenesulfonate, methyl p-toluenesulfonate, benzyl chloride, benzyl bromide, and substituted benzyl halides, such as p-chlorobenzyl chloride, p-nitrobenzyl chloride, p-methoxybenzyl chloride, o-chlorobenzyl chloride, and the like.

The quarternary ammonium salts are prepared by mixing the free base and ester of a strong acid in an inert solvent. Heating may be used to facilitate the reaction, although salt formation usually takes place readily at room temperature. The quaternary ammonium salt separates directly or can be obtained by concentration of the solution.

It is also possible to convert one quaternary ammonium salt to another in which the anion is different. If the anion of the original quaternary salt forms a water-insoluble silver salt the quaternary salt will react with silver oxide in aqueous medium to form the corresponding quaternary ammonium hydroxide, the original anion being removed as a precipitate. The quaternary ammonium hydroxide solution can then be neutralized with any desired acid, weak or strong, to produce a new quaternary ammonium salt in which the anion is different from that of the original salt. In this way quaternary ammonium salts in which the anion is derived from a weak acid can be prepared.

According to the bove processes, there are obtained, for example, the following N-substituted heterocyclic derivatives.

1-[γ-(phenylthio)-propyl]-4-(o-methoxyphenyl)- piperazine
1-[γ-(p-Fluorophenylthio)-propyl]-4-(o-methoxyphenyl)piperazine
1-[γ-(p-Tolylthio)-propyl]-4-(o-methoxyphenyl)piperazine
1-[γ-(p-Methoxyphenylthio)-propyl]-4-(o-methoxyphenyl)piperazine
1-[γ-(p-Trifluoromethylphenylthio)-propyl]-4-(o-methoxyphenyl)piperazine
1-[γ-(p-Nitrophenylthio)-propyl]-4-(o-methoxyphenyl)piperazine
1-[γ-(p-Fluorophenylthio)-propyl]-4-(o-methoxy-m-chlorophenyl)piperazine
1-[γ-(p-Fluorophenylthio)-butyl]-4-(p-methoxyphenyl)piperazine
1-[γ-(p-Fluorophenylthio)-propyl]-4-(p-trifluorophenyl)piperazine
1-[γ-(p-Fluorophenylthio)-propyl]-4-phenylpiperazine
1-[γ-(p-Fluorophenylthio)-propyl]-4-benzylpiperazine
1-[γ-(p-Fluorophenylthio)-propyl]-4-phenethylpiperazine
1-[γ-(p-Chlorophenylthio)-propyl]-4-benzylpiperazine
1-[γ-(p-Chlorophenylthio)-propyl]-4-phenethylpiperazire
1-[γ-(Phenylthio)-propyl]-4-benzylpiperazine
1-[γ-(Phenylthio)-butyl]-4-benzylpiperazine
1-[γ-(Phenylsulfinyl)-propyl]-4-(o-methoxyphenyl)piperazine
1-[γ-(p-Fluorophenylsulfinyl)-propyl]-4-(o-methoxyphenyl)piperazine
1-[γ-( p-Tolylsulfinyl)-propyl)-4-(o-methoxyphenyl)-piperazine
1-[γ-(p-Methoxyphenylsulfinyl)-propyl]-4-(o-methoxyphenyl)piperazine
1-[γ-(p-Trifluoromethylphenylsulfinyl)-propyl]-4-(p-methoxyphenyl)piperazine
1-[γ-(p-Nitrophenylsulfinyl)-propyl]-4-(o-methoxyphenyl)piperazine
1-[γ-(p-Fluorophenylsulfinyl)-propyl]-4-(o-methoxy-m-chlorophenyl)piperazine
1-[γ-(p-Fluorophenylsulfinyl)-butyl]-4-(o-methoxyphenyl)piperazine
1-[γ-(p-Fluorophenylsulfinyl)-propyl]-4-(p-trifluorophenyl)piperazine
1-[γ-(p-Fluorophenylsulfinyl)-propyl]-4-phenylpiperazine
1-[γ-(p-Fluorophenylsulfinyl)-propyl]-4-benzylpiperazine
1-[γ-(p-Fluorophenylsulfinyl)-propyl]-4-phenethylpiperzine
1-[γ-(p-Chlorophenylsulfinyl)-propyl]-4-benzylpiperazine
1-[γ-(p-Chlorophenylsulfinyl)-propyl]-4-phenethylpiperazine
1-(γ-Phenylsulfinyl-propyl)-4-benzylpiperazine
1-(γ-Phenylsulfinyl-butyl)-4-benzylpiperazine
1-[γ-(p-Fluorophenylsulfonyl)-propyl]-4-(o-methoxyphenyl)piperazine
1-[γ-(p-Tolylsulfonyl)-propyl]-4-(o-methoxyphenyl)-piperazine
1-[γ-(p-Fluorophenylsulfonyl)-propyl]-4-(o-methoxy-m-chlorophenyl)piperazine
1-[γ-(p-Fluorophenylsulfonyl)-propyl]-4-(p-trifluorophenyl)piperazine
1-[γ-(p-Fluorophenylthio)-propyl]-4-hydroxy-4-(p-chlorophenyl)piperidine
1-[γ-(p-Nitrophenylthio)-propyl]-4-hydroxy-4-(p-chlorophenyl)piperidine
1-[γ-(p-Fluorophenylthio)-propyl]-4-hydroxy-4-(m-trifluoromethylphenyl)piperidine 1-[γ-(p-Fluorophenylthio)-propyl]-4-hydroxy-4-(p-tolyl)piperidine
1-[γ-(p-Fluorophenylthio)-propyl]-4-carbamoyl-4-(1'-piperidyl)piperidine
1-[γ-(p-Chlorophenylthio)-propyl]piperidine
1-[γ-(p-Fluorophenylsulfinyl)-propyl]-4-hydroxy-4-(p-chlorophenyl)piperidine
1-[γ-(p-Fluorophenylsulfinyl)-propyl]-4-hydroxy-4-(m-trifluoromethylphenyl)piperidine
1-[γ-(p-Fluorophenylsulfinyl)-propyl]-4-carbamoyl-4-(1'-piperidyl)piperidine
1-[γ-(p-Chlorophenylsulfinyl)-propyl]piperidine
1-[γ-(p-Fluorophenylsulfonyl)-propyl]-4-hydroxy-4-(p-chlorophenyl)piperidine
1-[γ-(p-Tolylsulfonyl)-propyl]-4-hydroxy-4-(p-chlorophenyl)piperidine
1-[γ-(p-Fluorophenylsulfonyl)-propyl]-4-hydroxy-4-(m-trifluoromethylphenyl)piperidine
1-[γ-(p-Fluorophenylsulfonyl)-propyl]-4-carbamoyl-4-(1'-piperidyl)piperidine
1-[γ-(p-Fluorophenylsufonyl-propyl]-4-(N,N-dimethylcarbamoyl)-4-(p-chlorophenyl)piperidine This invention is further disclosed in the following Examples of more preferred embodiments thereof, which are presented for the purpose of illustration and it is not intended to limit the scope of the invention.

EXAMPLE 1

A mixture of 2.25 g. of 1-(p-fluorophenylthio)-3-chloropropane, 1.76 g. of 1-benzylpiperazine, 0.52 g. of sodium carbonate and 25 ml. of dimethylformamide is heated for four hours at a temperature of 80°–90°C. After the reaction mixture has been cooled, a mixture of 80 ml. of benzene and 100 ml. of water is added thereto. The aqueous layer is separated and extracted with 40 ml. of benzene. The organic layers are combined, washed with 50 ml. of water, dried over sodium sulfate and evaporated under reduced pressure. The oily residue is dissolved in ether and treated with ethanolic hydrogen chloride under cooling. The precipitate is collected by filtration and dried to give 1-[γ-(p-fluorophenylthio)-propyl]-4-benzylpiperazine dihydrochloride, m.p.: 231°–233°C. (decomp.). Recrystallization from ethanol gives white crystals, m.p.: 238.5°–239.5°C. (decomp.)

The following compounds are obtained in accordance with the manner similar to that of Example 1:

1-[γ-(p-Fluorophenylthio)-propyl]-4-(o-methoxyphenyl)piperazine dihydrochloride, m.p.: 204° – 205°C. (decomp.)
1-[γ-(p-Fluoropheylthio)-propyl]-4-(2'-methoxy-4'-chlorophenyl)piperazine dihydrochloride, m.p.: 199.5° – 201°C. (decomp.)
1-[γ-(p-Fluorophenylthio)-propyl]-4-phenethylpiperazine dihydrochloride, m.p.: 270° – 271.5°C. (decomp.)
1-[γ-(p-Nitrophenylthio)-propyl]-4-(o-methoxyphenyl)piperazine, m.p.: 89° – 91°C.
1-[γ-(p-Chlorophenylthio)-propyl]-4-benzylpiperazine dihydrochloride, m.p.: 244° – 244.5°C. (decomp.)
1-[γ-(p-Chlorophenylthio)-propyl]-4-phenethylpiperazine dihydrochloride, m.p.: 268° – 269°C. (decomp.)
1-[γ-(Phenylthio)-propyl]-4-benzylpiperazine dihydrochloride, m.p.: 244° – 245°C. (decomp.)
1-[γ-(p-Fluorophenylthio)-propyl]-4-hydroxy-4-(p-chlorophenyl)piperidine, m.p.: 123° – 124°C.
1-[γ-(p-Chlorophenylthio)-propyl]piperidine hydrochloride, m.p.: 157° – 158.5°C.
1-(γ-Phenylthio-butyl)-4-benzylpiperazine dihydrochloride, m.p.: 241° – 242.5°C. (decomp.)

EXAMPLE 2

A mixture of 2.46 g. of 1-(p-chlorophenylsulfinyl)-3-chloropropane, 0.9 g. of piperidine, 0.53 g. of sodium carbonate in 30 ml. of dimethylformamide is heated for 3 hours at a temperature of 80° – 87°C. After the reaction mixture has been cooled, a mixture of benzene and water is added thereto. The aqueous layer is separated and extracted with benzene. The organic layers are combined, washed with water, dried over sodium sulfate and evaporated under reduced pressure. The oily residue is dissolved in ether and treated with ethanolic hydrogen chloride under cooling. The precipitate is collected by filtration and dried to give 1-[γ-(p-chlorophenylsulfinyl)-propyl]piperidine hydrochloride, m.p.: 170° – 174°C. Recrystallization from benzene gives white crystals, m.p.: 176° – 177°C.

The following compounds are obtained in accordance with the manner similar to that of Example 2:

1-[γ-(p-Fluorophenylsulfinyl)-propyl]-4-(o-methoxyphenyl)piperazine dihydrochloride, m.p.: 173.5° – 175°C. (decomp.)
1-[γ-(p-Fluorophenylsulfinyl)-propyl]-4-benzylpiperazine dihydrochloride, m.p.: 213° – 214°C. (decomp.)
1[γ-(p-Fluoropheylsulfinyl)-propyl]-4-(2'-methoxy-4'-chlorophenyl)piperazine dihydrochloride, m.p.: 176.5° – 179°C. (decomp.)
1-[γ-(p-Nitrophenylsulfinyl)-propyl]-4-(o-methoxyphenyl)piperazine, m.p.: 145° – 146°C.
1-[γ-(p-Chlorophenylsulfinyl)-propyl]-4-benzylpiperazine dihydrochloride, m.p.: 220° – 221.5°C. (decomp.)
1-[γ-(p-Chlorophenysulfinyl)-propyl]-4-phenethylpiperazine dihydrochloride, m.p.: 224° – 225.5°C. (decomp.)
1-(δ-Phenylsulfinyl-butyl)-4-benzylpiperazine dihydrochloride, m.p.: 229.5° –231°C. (decomp.) 1-[γ-(p-Fluorophenylsulfinyl)-propyl]-4-hydroxy-4-(p-chlorophenyl)piperidine, m.p.: 123° – 124°C.

EXAMPLE 3

A mixture of 2.35 g. of 1-(p-chlorophenylsulfonyl)-3-chloropropane, 1.5 g. of 1-benzylpiperazine, 0.45 g. of sodium carbonate in 30 ml. of dimethylformamide is heated for 3 hours at a temperature of 85° – 90°C. After the reaction mixture has been cooled, a mixture of benzene and water is added thereto. The aqueous layer is separated and extracted with benzene. The organic layers are combined, washed with water, dried over sodium sulfate and evaporated under reduced pressure. The oily residue is dissolved in ether and treated with ethanolic hydrogen chloride under cooling. The precipitate is collected by filtration and dried to give 1-[γ-(p-chlorophenylsulfonyl)-propyl]-4-benzylpiperizine dihydrochloride, m.p.: 237° – 240°C. (decomp.) Recrystallization from ethanol gives white crystals, m.p.: 255.5° – 257°C. (decomp.)

The following compounds are obtained in accordance with the manner similar to that of Example 3:

1-[γ-(p-Fluorophenylsulfonyl)-propyl]-4-(o-methoxy-m-chlorophenyl)piperazine dihydrochloride, m.p.: 186° – 187.5°C.

1-[γ-(p-Fluorophenylsulfonyl)-propyl]-4-(o-methoxyphenyl)piperazine dihydrochloride, m.p.: 131° – 133°C. (decomp.)

1-[γ-(p-Tolylsulfonyl)-propyl]-4-(o-methoxyphenyl)-piperazine dihydrochloride, m.p.: 211° – 213°C. (decomp.)

EXAMPLE 4

A solution of 1.3 g. of p-fluorothiophenol in 5 ml. of dimethylformamide is added dropwise to an ice-cooled suspension of 0.5 g. of 50 % sodium hydride in 5 ml. of dimethylformamide and the mixture is heated for one hour at a temperature of 40° – 50°C. After cooling, the resulting mixture is added dropwise to a mixture of 2.7 g. of 1-(γ-chloro-propyl)-4-(o-methoxyphenyl)piperazine in 20 ml. of benzene and heated for 1 hour at a temperature of 40° – 50°C. After the reaction mixture has been cooled, 100 ml. of water is added thereto, and the organic layer is separated and washed with water, dried over sodium sulfate and evaporated under reduced pressure. The oily residue is dissolved in ether and treated with ethanolic hydrogen chloride under cooling. The precipitate is collected by filtration and dried to give 1-[γ-(p-fluorophenylthio)-propyl]-4-(o-methoxyphenyl)piperazine dihydrochloride, m.p.: 201° – 203°C. (decomp.) Recrystallization from ethanol given white crystals, m.p.: 204° – 205°C. (decomp.)

The following compounds are obtained in accordance with the manner similar to that of Example 4:

1-[γ-(p-Fluorophenylthio)-propyl]-4-(2'-methoxy-4'-chlorophenyl)piperazine dihydrochloride m.p.: 199.5° – 201°C. (decomp.)

1-[γ-(p-Fluorophenylthio)-propyl]-4-benzylpiperazine dihydrochloride, m.p.: 238.5° – 239.5°C. (decomp.)

1-[γ-(p-Fluorophenylthio)-propyl]-4-phenethylpiperazine dihydrochloride, m.p.: 270° – 271.5°C. (decomp.)

1-[γ-(p-Nitrophenylthio)-propyl]-4-(o-methoxyphenyl)piperazine, m.p.: 89° – 91°C.

1-[γ-(p-Chlorophenylthio)-propyl]-4-benzylpiperazine dihydrochloride, m.p.: 244° – 244.5°C. (decomp.)

1-]γ-(p-Chlorophenylthio)-propyl]-4-phenethylpiperazine dihydrochloride, m.p.: 268° – 269°C. (decomp.)

1-[γ-(Phenylthio)-propyl]-4-benzylpiperazine dihydrochloride, m.p.: 244° – 245°C. (decomp.)

1-[γ-(p-Fluorophenylthio)-propyl]-4-hydroxy-4-(p-chlorophenyl)piperidine, m.p.: 123° – 124°C.

1-[γ-(p-Chlorophenylthio)-propyl]piperidine hydrochloride, m.p.: 157° – 158.5°C.

1-[γ-(Phenylthio)-butyl]-4-benzylpiperazine dihydrochloride, m.p.: 241° – 242.5°C. (decomp.)

EXAMPLE 5

To a mixture of 0.8 g. of lithium aluminum hydride in 30 ml. of tetrahydrofuran is added dropwise a solution of 1.5 g. of 1-(4'-phenylthio-butyryl)-4-benzylpiperazine in 5 ml. of tetrahydrofuran. The mixture is refluxed for ten hours. To the reaction mixture cooled in ice, is gradually added 30 ml. of water and the precipitate is filtered off. The filtrate is concentrated to one-third in volume, and extracted with benzene. The organic layer is washed with water, dried over sodium sulfate and evaporated under reduced pressure. The oily residue is dissolved in ether and treated with ethanolic hydrogen chloride under cooling. The precipitate is collected by filtration and dried to give 1-(δ-phenylthio-butyl)-4-benzylpiperazine dihydrochloride, m.p.: 232° – 234°C. (decomp.) Recrystallization from ethanol gives white crystals, m.p.: 241° – 242.5°C. (decomp.)

The following compounds are obtained in accordance with the manner similar to that of Example 5:

1-[γ-(p-Fluorophenylthio)-propyl]-4-(o-methoxyphenyl)piperazine dihydrochloride, m.p.: 204° – 205°C. (decomp.)

1-[γ-(p-Fluorophenylthio)-propyl]-4-(2'-methoxy-4'-chlorophenyl)piperazine dihydrochloride, m.p.: 199.5° – 201°C. (decomp.)

1-[γ-(p-Fluorophenylthio)-propyl]-4-benzylpiperazine dihydrochloride, m.p.: 238.5° – 239.5°C. (decomp.)

1-[γ-(p-Fluorophenylthio)-propyl]-4-phenethylpiperazine dihydrochloride, m.p.: 270° – 271.5°C. (decomp.)

1-[γ-(p-Chlorophenylthio)-propyl]-4-benzylpiperazine dihydrochloride, m.p.: 244° – 244.5°C. (decomp.)

1-[γ-(p-Chlorophenylthio)-propyl]-4-phenethylpiperazine dihydrochloride, m.p.: 268° – 269°C. (decomp.)

1-(γ-Phenylthio-propyl)-4-benzylpiperazine dihydrochloride, m.p.: 244° – 245°C. (decomp.)

1-[γ-(p-Fluorophenylthio)-propyl]-4-hydroxy-4-(p-chlorophenyl)piperidine, m.p.: 123° – 124°C.

1-[γ-(p-Chlorophenylthio)-propyl]piperidine hydrochloride, m.p.: 157° – 158.5°C.

EXAMPLE 6

A solution of 1.6 g. of p-fluorobenzenesulfinic acid in 5 ml. of dimethylformamide is added dropwise to an ice-cooled mixture of 0.5 g. of 50 % sodium hydride in 5 ml. of dimethylformamide and heated for one hour at a temperature of 40°C. After cooling, the resulting mixture is added dropwise to mixture of 2.7 g. of 1-(γ-chloropropyl)-4-(o-methoxyphenyl)piperazine in 20 ml. of benzene and heated for 1 hour at a temperature of 40°C. After cooling, 100 ml. of water is added, and the organic layer is separated and washed with water, dried over sodium sulfate and evaporated under reduced pressure. The oily residue is dissolved in ether and treated with hydrogen chloride under cooling. The precipitate is collected by filtration and dried to give 1-[γ-(p-fluorophenylsulfonyl)-propyl]-4-(o-methoxyphenyl)piperazine dihydrochloride, m.p.: 128° – 130°C. (decomp.) Recrystallization from ethanol gives white crystals, m.p.: 131° – 133°C. (decomp.)

The following compounds are obtained in accordance with the manner similar to that of Example 6:

1-[γ-(p-Fluorophenylsulfonyl)-propyl]-4-(o-methoxy-m-chlorophenyl)piperazine dihydrochloride, m.p.: 186° – 187.5°C. (decomp.)

1-[γ-(p-Chlorophenylsulfonyl)-propyl]-4-benzylpiperazine dihydrochloride, m.p.: 255.5° – 257°C. (decomp.)

1-[γ-(p-Tolylsulfonyl)-propyl]-4-(o-methoxyphenyl)piperazine dihydrochloride, m.p.: 211° – 213°C. (decomp.)

EXAMPLE 7

To a solution of 1.08 g. of 1-[γ-(p-fluorophenylthio)-propyl]-4-(o-methoxyphenyl)piperazine in 10 ml. of glacial acetic acid, is added dropwise 0.85 g. of 30 % aqueous hydrogen peroxide under cooling. The mixture is stirred for one hour at a temperature of 20° – 30°C. Then the reaction mixture is poured into 50 ml. of water, neutralized with aqueous ammonia and extracted with benzene. The organic layer is washed with water, dried over sodium sulfate and evaporated under reduced pressure. The oily residue is dissolved in ether and treated with ethanolic hydrogen chloride under cooling. The precipitate is collected by filtration and dried to give 1-[γ-(p-fluorophenylsulfinyl)-propyl]-4-(o-methoxyphenyl)piperazine dihydrochloride, m.p.: 170°–171.5°C. (decomp.) Recrystallization from ethanol gives white crystals, m.p.: 173.5° – 175°C. (decomp.)

The following compounds are obtained in accordance with the manner similar to that of Example 7:

1-[γ-(p-Fluorophenylsulfinyl)-propyl]-4-benzylpiperazine dihydrochloride, m.p.: 213° – 214°C. (decomp.)

1-[γ-(p-Fluorophenylsulfinyl)-propyl]-4-(2'-methoxy-4'-chlorophenyl)piperazine dihydrochloride, m.p.: 176.5° – 179°C. (decomp.)

1-[γ-(p-Nitrophenylsulfinyl)-propyl]-4-(o-methoxyphenyl)piperazine, m.p.: 145° – 146°C.

1-[γ-(p-Chlorophenylsulfinyl)-propyl]-4-benzylpiperazine dihydrochloride, m.p.: 220° – 221.5°C. (decomp.)

1-[γ-(p-Chlorophenylsulfinyl)-propyl]-4-phenethylpiperazine dihydrochloride, m.p.: 224° – 225.5°C. (decomp.)

1-(γ-Phenylsulfinyl-butyl)-4-benzylpiperazine dihydrochloride, m.p.: 229.5° – 231°C. (decomp.)

1-[γ-(p-Fluorophenylsulfinyl)-propyl]-4-hydroxy-4-(p-chlorophenyl)piperidine, m.p.: 123° – 124°C.

1-[γ-(p-Chlorophenylsulfinyl)-propyl]-piperidine hydrochloride, m.p.: 176° – 177°C.

What is claimed is:

1. A compound of the formula,

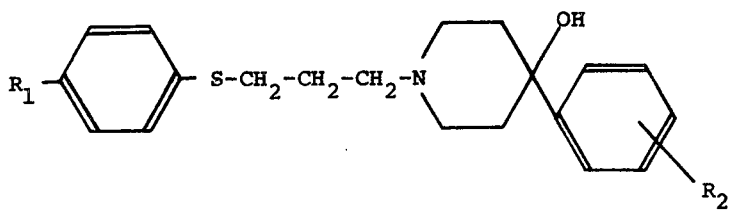

wherein $R_1$ is halogen and $R_2$ is hydrogen, halogen, nitro, trifluoromethyl, $C_1$-$C_7$ alkoxy or $C_1$-$C_7$ alkyl, or its non-toxic, pharmaceutically acceptable salt.

2. 1-[γ-(p-Fluorophenylthio)-propyl]-4-hydroxy-4-(p-chlorophenyl)piperidine or its non-toxic, pharmaceutically acceptable salt.

3. 1-[γ-(p-Fluorophenylthio)-propyl]-4-hydroxy-4-(m-trifluoromethylphenyl)-piperidine or its non-toxic, pharmaceutically acceptable salt.

* * * * *